(12) United States Patent
Boldewijn et al.

(10) Patent No.: US 7,247,854 B2
(45) Date of Patent: Jul. 24, 2007

(54) LIMITING DEVICE FOR ELECTROMAGNETIC RADIATION, NOTABLY IN AN ANALYSIS DEVICE

(75) Inventors: Jan Boldewijn, Vriezenveen (NL); Waltherus W. van den Hoogenhof, Almelo (NL)

(73) Assignee: PANalytical BV, Almelo (NL)

( * ) Notice: Subject to any disclaimer, the term of this patent is extended or adjusted under 35 U.S.C. 154(b) by 333 days.

(21) Appl. No.: 10/482,606

(22) PCT Filed: Jun. 20, 2002

(86) PCT No.: PCT/IB02/02479

§ 371 (c)(1),
(2), (4) Date: Jun. 18, 2004

(87) PCT Pub. No.: WO03/002996

PCT Pub. Date: Jan. 9, 2003

(65) Prior Publication Data

US 2004/0234035 A1    Nov. 25, 2004

(30) Foreign Application Priority Data

Jun. 29, 2001  (EP) .................................. 01202514

(51) Int. Cl.
*G21K 1/02* (2006.01)
(52) U.S. Cl. .................................. 250/363.01
(58) Field of Classification Search ............. 250/363.1
See application file for complete search history.

(56) References Cited

U.S. PATENT DOCUMENTS 6,653,645 B1 * 11/2003 Chen ....................... 250/492.3

FOREIGN PATENT DOCUMENTS

JP    62-226551    * 10/1987

* cited by examiner

*Primary Examiner*—David Porta
*Assistant Examiner*—Christine Sung
(74) *Attorney, Agent, or Firm*—Jensen & Puntigam PS

(57) ABSTRACT

A limiting device (9) for electromagnetic radiation (3; 5; 7) includes an essentially flat beam cross-section limiter (10) which partly or completely encloses at least one passage aperture (12; 13) for beams (5; 7) and is constructed so that it also includes at least one second beam cross-section limiter (14) which, in the active position, constitutes at least one longitudinal component extending at an angle to the first beam cross-section limiter (10).

Figure 1:
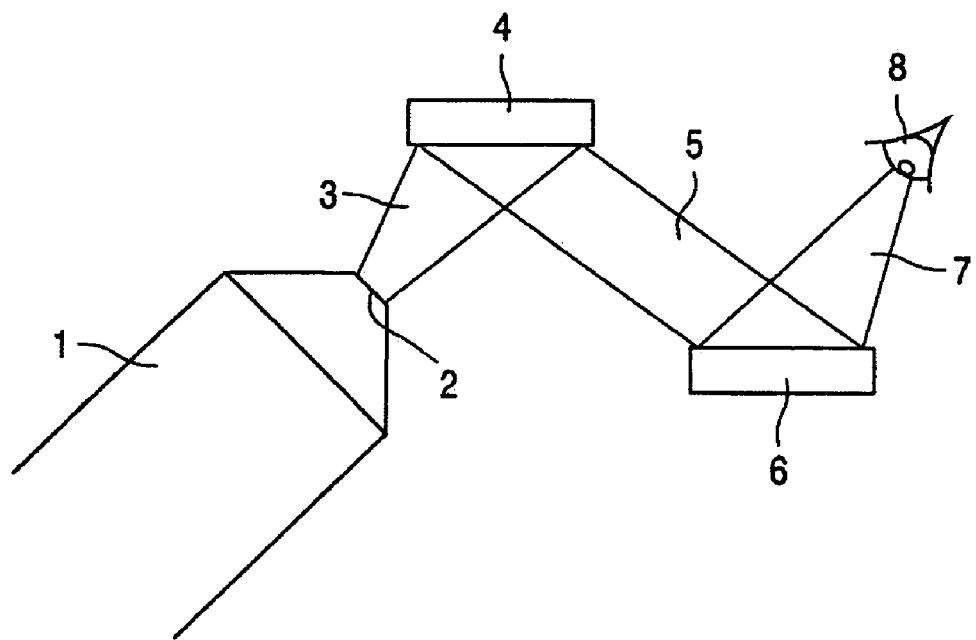

16 Claims, 4 Drawing Sheets a beam limiting device which can be clicked together, and

LIMITING DEVICE FOR ELECTROMAGNETIC RADIATION, NOTABLY IN AN ANALYSIS DEVICE

The invention relates to a limiting device for limiting the cross-section of a beam of electromagnetic rays as disclosed in the introductory part of claim 1, as well as to an analysis device for the examination of material samples by means of electromagnetic radiation as disclosed in the introductory part of claim 12.

For the analysis of material samples by means of electromagnetic radiation, for example, by means of X-rays, it is necessary to limit the cross-section of the beam which is incident on the sample as well as that of the beam which emanates from the sample so as to be incident on a detector; such beam limiting is necessary to avoid irradiation of parts which are situated to the side of the optical path, for example, parts of a sample holder, and to prevent radiation reflected by such parts or scattered or secondary radiation arising at that area from reaching the detector because such information would falsify the analysis result.

For example, in the case of an energy-dispersive measurement all photons incident on the detector are counted, regardless of whether such photons originate directly from the sample to be examined or from surrounding components.

Therefore, it is an object of the invention to enable an as genuine as possible measuring result to be obtained.

This object is achieved in accordance with the invention by means of a limiting device as disclosed in the characterizing part of claim 1 as well as by means of an analysis device as disclosed in the characterizing part of claim 12. Advantageous embodiments of the invention are disclosed in the dependent claims 2 to 11 and 13 to 16.

The second beam cross-section limiter, comprising a component extending at an angle relative to the longitudinal direction of the first beam cross-section limiter in accordance with the invention enables limitation of the beam cross-section of a beam which is incident on a sample as well as of a beam which is reflected thereby or produced by scattering or secondary processes and emanates therefrom. Unlike a two-dimensional diaphragm, whose entire cross-section is exposed to the incident beam and whose entire edge zone, therefore, produces reflected rays or secondary radiation, that is, by interaction of the incident rays with the diaphragm material, the second beam cross-section limiter enables partial masking of the first beam cross-section limiter. The interaction processes of the incident beam with the first beam cross-section limiter which is planar as a diaphragm, are thus limited to a part thereof. Consequently, fewer disturbing secondary rays are produced overall. It is at the same time possible for the second beam cross-section limiter to shield another region of the first beam cross-section limiter from the detector limiter in such a manner that reflected radiation or scattered or secondary radiation arising in this region cannot reach the detector because it is stopped by the second beam cross-section limiter.

When the first beam cross-section limiter comprises two mutually intersecting passage apertures for rays, it can be used as an integral component for an incident beam as well as for a beam which is emitted by a sample or a target. For example, when the second beam cross-section limiter is arranged so as to extend perpendicularly thereto in such a manner that it intersects the passage apertures of the first beam cross-section limiter at its edges of intersection, defined limiting edges are formed, that is, along its entire contour, for an incident beam or a beam returned by the sample or a target, the respective passage apertures of the first beam cross-section limiter and the passage aperture of the second beam cross-section limiter advantageously forming each time in projection substantially a circle or a similar regular geometrical contour configuration while the incident beam enters perpendicularly to the contour area thus formed between the first passage aperture of the first beam cross-section limiter and the passage aperture of the second beam cross-section limiter and the exit beam emanates in conformity with the defined contour between the second passage aperture of the first beam cross-section limiter and the passage aperture of the second beam cross-section limiter. The incident beam as well as the returned beam then encounter defined boundaries along their entire circumference, so that for both beams a geometrically regular contour configuration of the exposed region can be formed, that is, notably a circle. Rays which are outside this region are reliably stopped.

It is particularly advantageous to configure the contour of the passage aperture in such a manner that the incoming beam irradiates merely edge zones of its passage aperture provided for the entry and that those edge zones of the second passage aperture of the first beam cross-section limiter wherefrom secondary rays could mingle with the returned beam, are not exposed by the measuring beams. At the same time it is particularly advantageous that the radiation arising at the first passage window of the first beam cross-section limiter, notably secondary radiation which is caused by interaction processes and is emitted in the direction of the emanating beam, is shielded by the second beam cross-section limiter so that it cannot reach the detector. Overall the number of photons which arise from secondary processes and reach the detector is thus significantly reduced, so that the measuring result is significantly enhanced.

Figure 2:
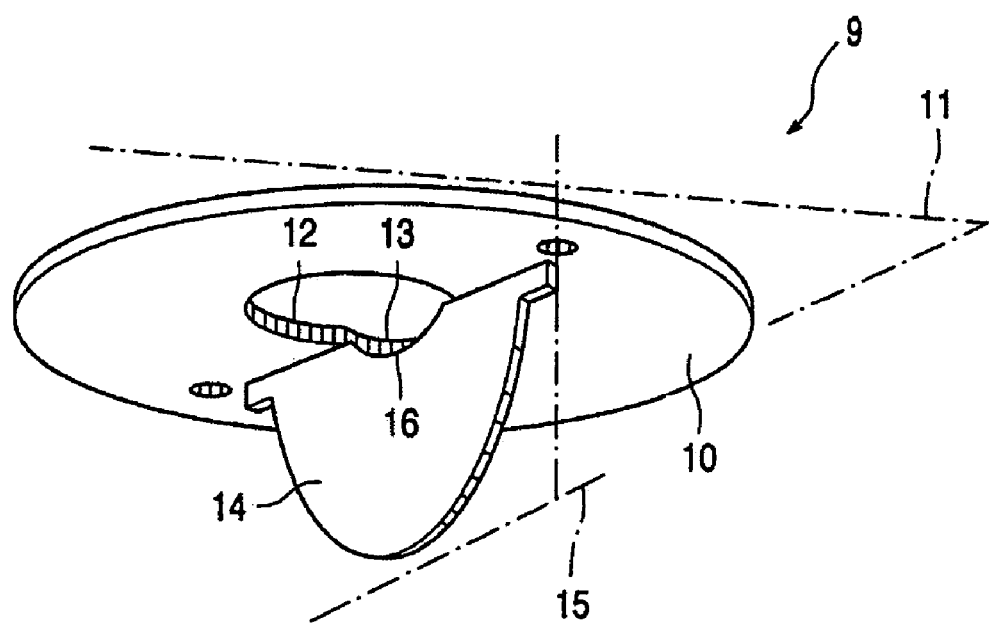
Figure 3:
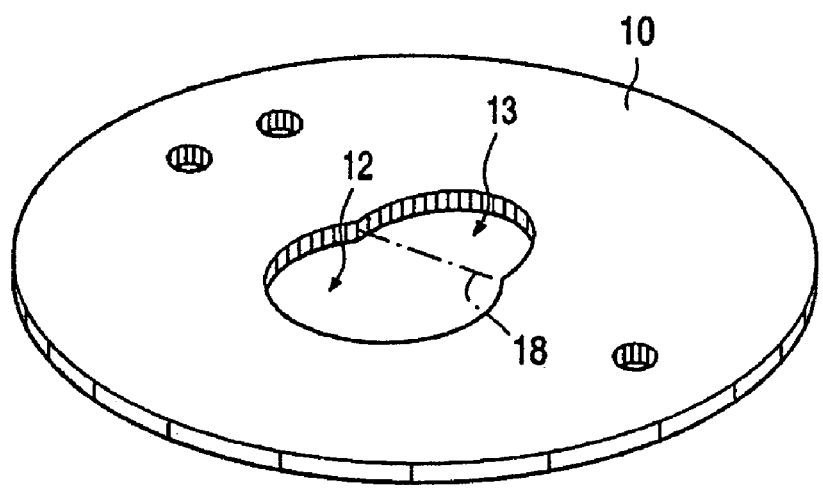
Figure 4:
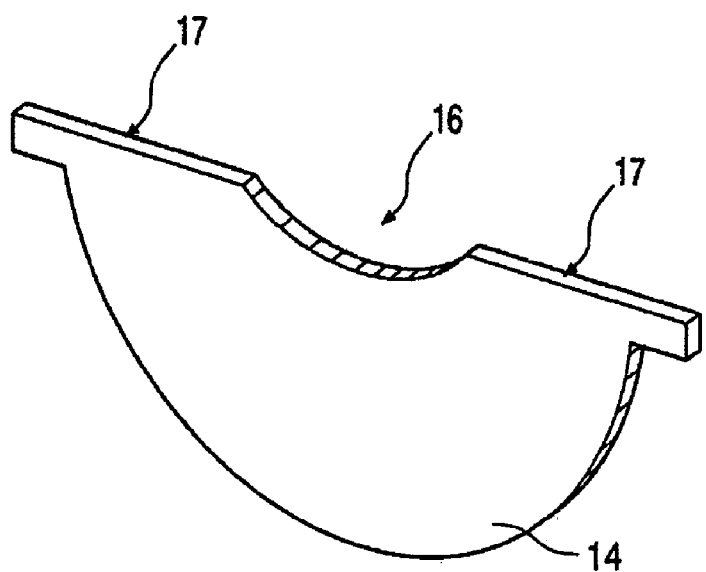
Figure 5:
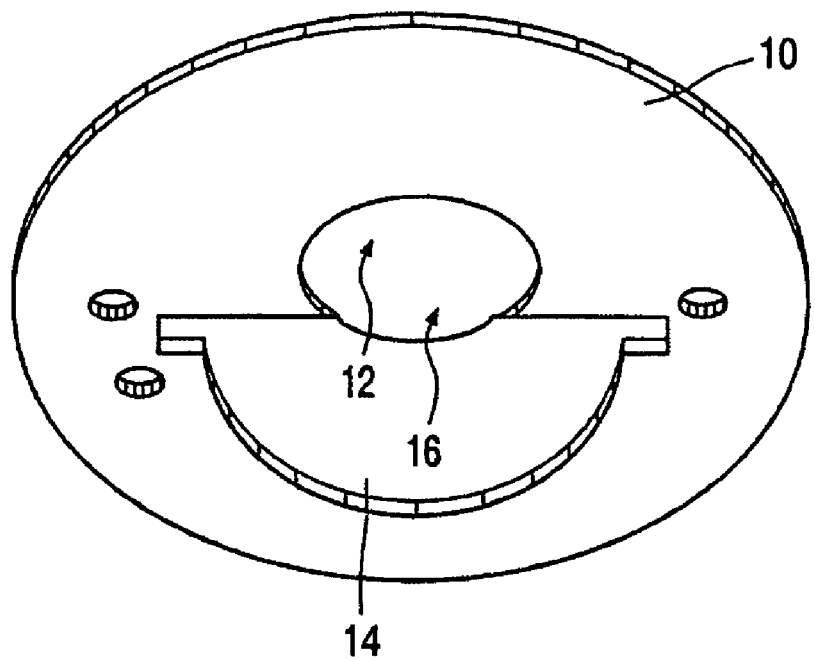
Figure 6:
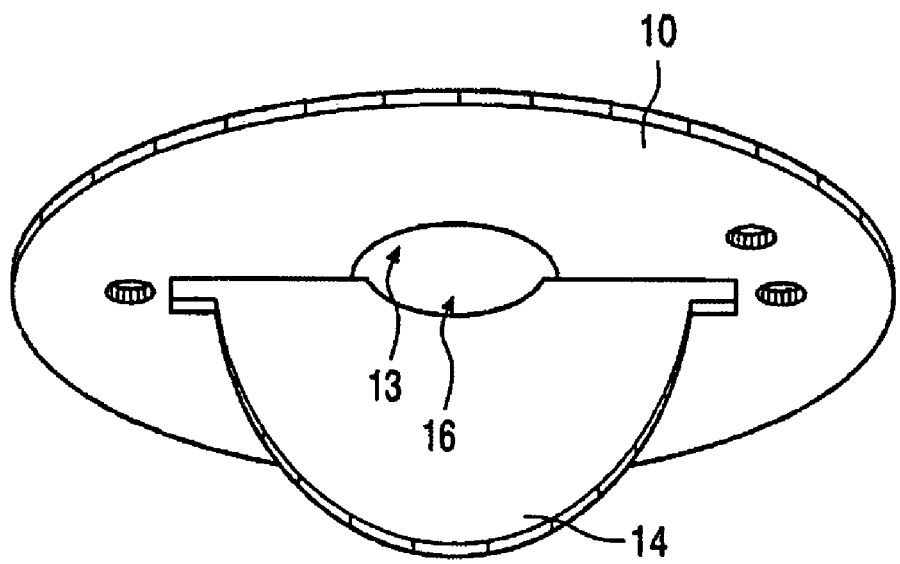
Figure 7:
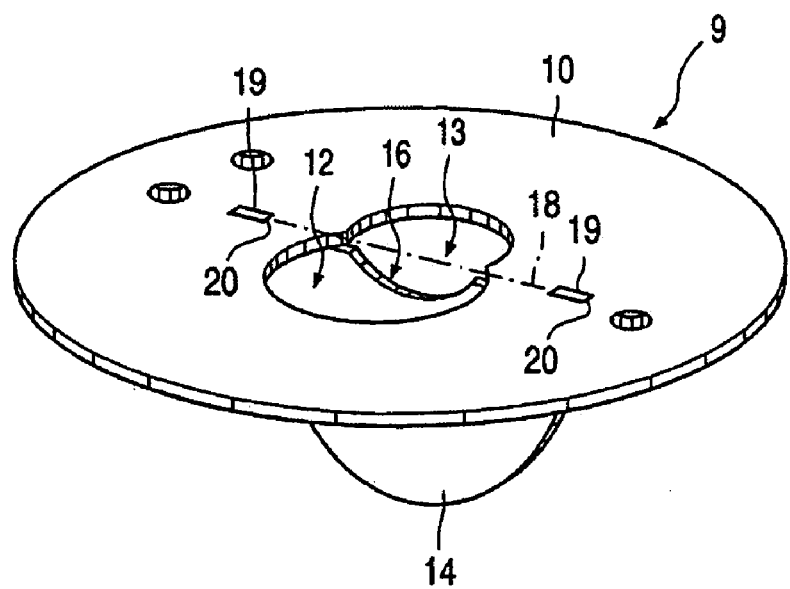
Figure 8:
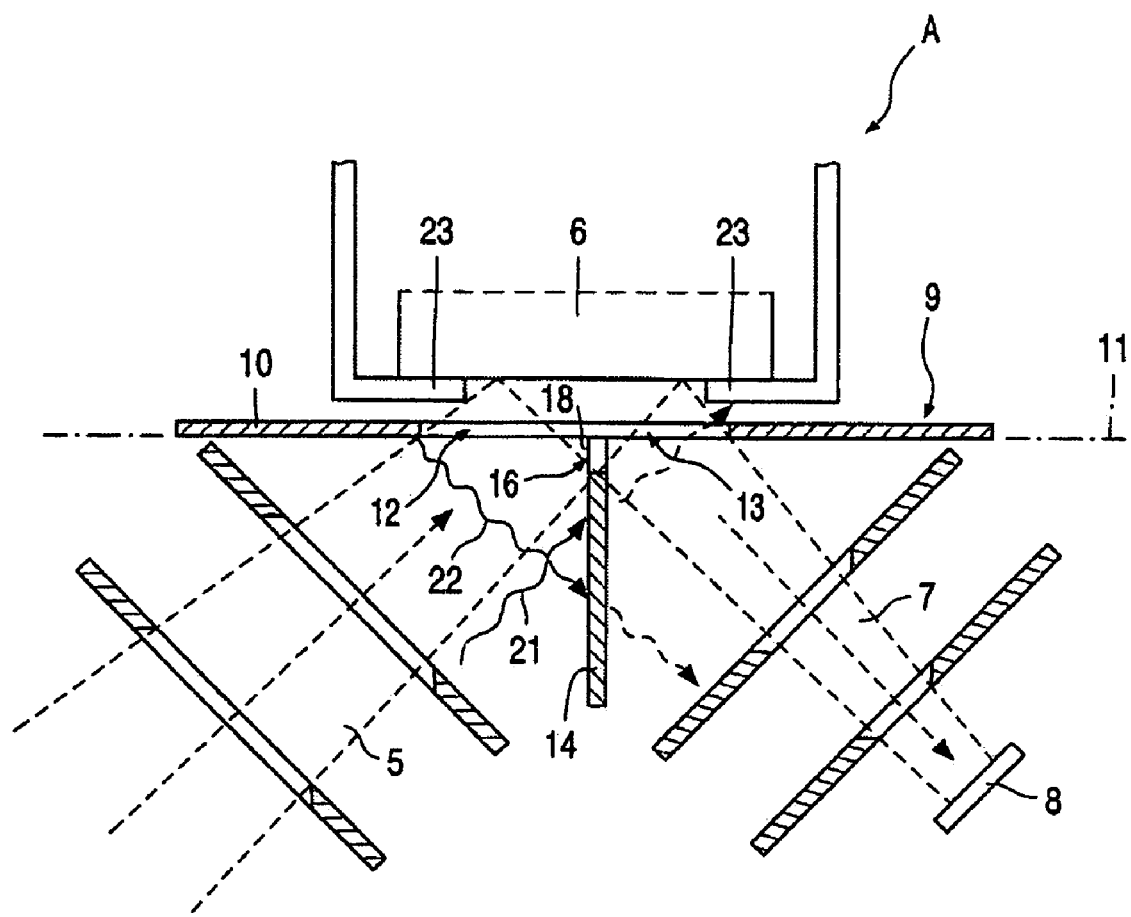

Further advantages and details of the invention will become apparent from the embodiments of the invention which are described hereinafter and shown in the drawing. In the drawing:

FIG. 1 shows a basic beam path as it occurs during the examination of a sample by means of X-rays, FIG. 2 is a perspective view of the beam limiting device in accordance with the invention, FIG. 3 is a partial perspective view of the first beam cross-section limiter extending in the first plane, FIG. 4 is a view, similar to that of FIG. 3, of the second beam cross-section limiter which extends in the plane directed perpendicularly thereto, FIG. 5 is a perspective view of the beam cross-section limiter in accordance with the invention as viewed along the light beam incident on the sample, FIG. 6 is a view, similar to that of FIG. 5, as viewed from the detector, FIG. 7 is a view, similar to that of FIG. 2, of a beam limiting device which can be clicked together, and FIG. 8 is a cross-sectional view of the beam path of the incident beam and the beam emanating from the sample when the device in accordance with the invention is inserted.

The present embodiment will be described in detail with reference to the beam path shown in FIG. 1. It will be evident that other beam paths and radiation sources as well as other arrangements of samples to be examined are also feasible. The configuration shown in FIG. 1 utilizes a radiation source 1, in this case being an X-ray source, and a first beam 3 emanates from the exit window 2 thereof, which beam is conducted to a target 4 so as to obtain the characteristic radiation of the target material in the beam which is reflected thereby or formed by interaction processes. The beam 5, therefore, serves as a measuring beam and is partly reflected by the sample 6 to be examined, the angle of incidence usually being equal to the angle of reflection. Moreover, scattering and secondary rays are caused by interaction processes between the measuring beam 5 and the sample 6; these scattering and secondary rays are taken up in the beam 7 which emanates from the sample 6 and is directed onto the detector 8.

As is shown in FIG. 8 and as will be described in detail hereinafter, the limiting device 9 for limiting the cross-section in accordance with the invention is arranged between the incident measuring beam 5 and the beam 7 to the detector in front of the sample 6. The limiting device 9 for the beam cross-section of the electromagnetic rays includes a first beam cross-section limiter 10 which extends in a plane 11 and bounds two mutually intersecting passage apertures 12, 13 in the present embodiment.

The limiting device 9 also includes a second beam cross-section limiter 14 which extends in a plane 15 in the present embodiment, which plane is directed perpendicularly to the first plane 11 of the first beam cross-section limiter 10.

It is not necessary that the elements 14 and 10 extend perfectly perpendicularly to one another; it may suffice when the element 14 instead comprises a longitudinal component which extends at an angle relative to the plane 11 of the first beam cross-section limiter 10. The perpendicular orientation offers the advantage that the use of a single structural component for the second beam cross-section limiter 14 enables an effect to be exerted on the incident beam 5 as well as a similar effect on the exit beam 7. This effect can in principle also be achieved by means of a plurality of structural components 14 which may be arranged adjacent one another and parallel to one another or at an angle relative to one another.

The device 9 may be constructed as a single piece or as a device consisting of a number of pieces and be made of, for example, a metal such as tungsten. When the limiting device 9 consists of two pieces, a detachable connection is possible between the parts 10 and 14, for example, in that the second beam cross-section limiter 14 can be retained in recesses 20 of the first beam cross-section limiter 10 by way of projections 19. A connection by way of screws, clamps or other positive locking connection elements is also feasible. It is also possible, for example, to insert the second beam cross-section limiter 14 first in an analysis device A, for example, in a holding groove, after which the first beam cross-section limiter can be arranged merely loosely thereon. Corresponding mounts in the analysis device A then ensure that the alignment of the parts 10 and 14 relative to one another is automatically correct.

In order to enable the use for incoming as well as outgoing beams 5, 7, the first beam cross-section limiter 10 is provided with two passage apertures 12, 13 which intersect one another along an imaginary line of intersection 18. This line of intersection 18 is situated in the plane 15 in which the second beam cross-section limiter 14 is situated in the present embodiment. It comprises a passage aperture 16 for the rays, for example, X-rays (FIG. 4), which passage aperture starts from its edge zone 17 and is only partly enclosed.

When the parts 10 and 14 are attached to one another, the passage apertures 12, 13 are intersected by the second beam cross-section limiter 14 along their line of intersection 18, so that the passage aperture 16 in the plane 15 extends perpendicularly to the passage apertures 12 and 13 and supplements these apertures each time so as to form a closed contour. This closed contour is shown in FIG. 5 for the incident beam 5 and in FIG. 6 for the exit beam 7 and forms each time substantially a circle in a projection perpendicular to the direction of propagation of the beams 5 and 7, respectively. However, it is also possible for the passage apertures 12, 13 as well as 16 to have a different contour geometry, for example, a square or rectangular contour. In that case, for example, for the incident beam 5 through the first passage aperture 12 of the first beam cross-section limiter 10 and the passage aperture 16 of the second beam cross-section limiter 14 there would be obtained a square or a rectangular entrance aperture, and also for the exit beam 7 formed by the second passage aperture 13 of the first beam cross-section limiter 10 and the passage aperture 16 of the second beam cross-section limiter 14.

The limiting device 9 is mounted in the analysis device A in such a manner that it is positioned in front of a front surface of a sample 6 to be irradiated. The sample 6 is supported, for example by a sample holder 23 (FIG. 8).

The second beam cross-section limiter 14 yields a double effect in respect of the removal of disturbing rays: on the one hand, rays 21 which are incident on the sample holder 23 or the edge zone of the second passage aperture 13 of the first beam cross-section limiter 10 and hence may give rise to undesirable secondary processes are eliminated, because they are stopped by the second beam cross-section limiter 14 and cannot traverse the comparatively small passage aperture 16 (denoted in FIG. 8 by wavy lines 21 in front of the second beam cross-section limiter 14 and by dashed wavy lines therebehind). On the other hand, rays 22 which are reflected on the edges of the first passage aperture 12 of the first beam cross-section limiter 10 or on the sample holder 23, or scattered or secondary rays caused by interaction processes, are stopped by the second beam cross-section limiter 10 (denoted in FIG. 8 by a wavy line in front of the second beam cross-section limiter 14 and by a dashed wavy line 22 behind said limiter).

As is apparent from the dashed straight lines within the beams 5 and 7, the edges of the passage apertures 12, 13 and 16 also serve for edge limiting of the incident beam 5 and the exit beam 7. A typical dimension of the diameter of the light spot on the sample amounts to approximately 20 mm.

Overall it is thus achieved that the incident beam is kept completely remote from the second passage aperture 13 in the first beam cross-section limiter 10, so that it cannot cause any secondary processes at the area thereof. The width of the incident beam 5 is limited on the one hand by the first passage aperture 12 in the first beam cross-section limiter 10 and on the other hand by the passage aperture 16 in the second beam cross-section limiter 14.

It is also ensured that no reflected or secondary rays 22 from the first passage aperture 12 can invade the beam 7, because these rays are completely stopped. Therefore, the detector 8 receives only rays which in any case have not arisen in the edge zone of the first passage aperture 12.

Secondary rays reflected by the sample holder 23 or the diaphragm material of the first beam cross-section limiter 10 or produced by interaction, therefore, are very effectively prevented from having an effect on the measuring result.

The invention claimed is:

1. A limiting device (9) for limiting electromagnetic radiation (3;5;7), which device includes an essentially flat beam cross-section limiter (10) which at least partly encloses at least one passage aperture (12;13) for beams (5;7), characterized in that the device (9) includes at least a second beam cross-section limiter (14) which, in the active position, constitutes at least one component extending at an angle, which is not zero, to the first beam cross-section limiter (10).

2. A device as claimed in claim 1, characterized in that the second beam cross-section limiter (14) extends perpendicularly to the first beam cross-section limiter (10).

3. A device as claimed in claim 1, characterized in that the first beam cross-section limiter (10) includes two mutually intersecting passage apertures (12;13) for beams (5;7).

4. A device as claimed in claim 1, characterized in that the second beam cross-section limiter (14) includes a passage aperture (16) for beams (5;7) which commences in an edge zone and is only partly enclosed.

5. A device as claimed in claim 1, characterized in that the passage apertures (12;13;16) of the first and the second beam cross-section limiter (10;14) are formed by respective sectors of a circle.

6. A device as claimed in claim 1, characterized in that the first passage aperture (12) of the first beam cross-section limiter (10) constitutes in projection at least approximately a circle in conjunction with the passage aperture (16) of the second beam cross-section limiter (14).

7. A device as claimed in claim 6, characterized in that the circular contour is such that a beam (5) which enters perpendicularly thereto reaches only edge faces of the first passage aperture (12) of the first beam cross-section limiter (10) as well as the passage aperture (16) of the second beam cross-section limiter (14).

8. A device as claimed in claim 1, characterized in that the second passage aperture (13) of the first beam cross-section limiter (10) constitutes in projection a circle in conjunction with the passage aperture (16) of the second beam cross-section limiter (14).

9. A device as claimed in claim 8, characterized in that the circular contour is such that a beam (7) which is incident on or emanates from this contour at right angles reaches only edge zones of the second passage aperture (13) of the first beam cross-section limiter (10) as well as the passage aperture (16) of the second beam cross-section limiter (14), and that reflected or secondary rays (22) which originate from boundaries of the first passage aperture (12) of the first beam cross-section limiter (10) do not invade the beam (7) emanating from said passage apertures (13;16).

10. A device as claim in claim 1, characterized in that the fist beam cross-section limiter (10) and the second beam cross-section limiter (14) can be detachably connected to one another.

11. An analysis device (A) for the examination of material samples (6) by means of electromagnetic radiation (3; 5; 7), characterized in that the analysis device (A) includes at least one limiting device (9) as claimed in claim 1.

12. An analysis device as claimed in claim 11, characterized in that the limiting device (9) is built into the analysis device (A) in such a manner that a beam (5) which is incident on an optical element, and directed onto a sample (6) passes through the aperture of incidence which is enclosed by the boundaries of the first passage aperture (12) of the first beam cross-section limiter (10) and the boundary of the passage aperture (16) of the second beam cross-section limiter (14) and that a beam (7) which originates from the optical element, traverses the exit aperture which is limited by the boundaries of the second passage aperture (13) of the first beam cross-section limiter (10) and the passage aperture (16) of the second beam cross-section limiter (14).

13. An analysis device as claimed in claim 12, characterized in that the incident beam (5;21) contacts merely edge zones of the first passage aperture (12) of the first beam cross-section limiter (10) and the passage aperture (16) of the second beam cross-section limiter (14).

14. An analysis device as claimed in claim 12, characterized in that secondary rays (22) which are reflected by the first passage aperture of the first beam cross-section limiter (10) or are produced at that area do not traverse the exit aperture formed by the second passage aperture (13) of the first beam cross-section limiter (10) and the passage aperture (16) of the second beam cross-section limiter (14).

15. An analysis device as claimed in claim 11, characterized in that the first passage aperture (12) and the second passage aperture (13) of the first beam cross-section limiter (10) are of different size.

16. A limiting device (9) for limiting electromagnetic radiation (3;5;7), which device includes an essentially flat beam cross-section limiter (10) which at least partly encloses two mutually intersecting passage apertures (12; 13) for beams (5;7), characterized in that the device (9) includes a second beam cross-section limiter (14) which includes a passage aperture (16) far beams (5;7) which commences in an edge zone and is only partly enclosed.

\* \* \* \* \*